US010744341B2

(12) United States Patent
Johnson et al.

(10) Patent No.: US 10,744,341 B2
(45) Date of Patent: Aug. 18, 2020

(54) SYSTEM AND METHOD FOR DIRECTING LIGHT INTO A PATIENTS EYE (71) Applicant: MULTI RADIANCE MEDICAL, Solon, OH (US)

(72) Inventors: Douglas Johnson, Brownstown, MI (US); Max Kanarsky, Solon, OH (US); Larry W. Finn, Georgetown, TX (US); Ian Dwayne Campbell, Saginaw, TX (US); Jeffrey A. Lenk, Hutto, TX (US); Michael T. Barrett, Georgetown, TX (US); Scott R. Lenk, Taylor, TX (US)

(73) Assignee: MULTI RADIANCE MEDICAL, Solon, OH (US)

( * ) Notice: Subject to any disclaimer, the term of this patent is extended or adjusted under 35 U.S.C. 154(b) by 0 days.

(21) Appl. No.: 16/317,984

(22) PCT Filed: Aug. 2, 2018

(86) PCT No.: PCT/US2018/044954
§ 371 (c)(1),
(2) Date: Jan. 15, 2019

(87) PCT Pub. No.: WO2019/028222
PCT Pub. Date: Feb. 7, 2019

(65) Prior Publication Data
US 2020/0086135 A1 Mar. 19, 2020

Related U.S. Application Data (60) Provisional application No. 62/540,204, filed on Aug. 2, 2017.

(51) Int. Cl.
*A61N 5/06* (2006.01)
*A61N 5/067* (2006.01)

(52) U.S. Cl.
CPC ...... *A61N 5/0613* (2013.01); *A61N 2005/067* (2013.01); *A61N 2005/0626* (2013.01);
(Continued)

(58) Field of Classification Search
CPC ...... A61N 5/06; A61N 5/0613; A61N 5/0622; A61N 2005/002; A61N 2005/005;
(Continued)

(56) References Cited

U.S. PATENT DOCUMENTS 2,389,223 A * 11/1945 Werner
4,858,609 A     8/1989 Cole
(Continued)

FOREIGN PATENT DOCUMENTS

RU     2297813 C1     4/2007
WO     2008127204 A1     10/2008
(Continued)

OTHER PUBLICATIONS

International Search Report and Written Opinion dated Oct. 23, 2018 for Application No. PCT/US2014/044954.
(Continued)

*Primary Examiner* — Eugene T Wu
(74) *Attorney, Agent, or Firm* — Tarolli, Sundheim, Covell & Tummino LLP (57) ABSTRACT Disorders of the eye can be treated by photobiomodulation therapy according to a device designed to direct light into a patient's eye, no matter the configuration of the eye. The device, including a printed circuit board that includes an array of light delivery devices and a heat sink lens, can be placed proximal to the patient's eye. The light delivery devices can be powered to generate light. The light can be directed into the patient's eye regardless of a position of the patient's eye.

16 Claims, 5 Drawing Sheets

(52) U.S. Cl.
CPC ............... *A61N 2005/0648* (2013.01); *A61N 2005/0652* (2013.01); *A61N 2005/0659* (2013.01); *A61N 2005/0663* (2013.01)

(58) Field of Classification Search
CPC .... A61N 2005/0632; A61N 2005/0635; A61N 2005/0642; A61N 2005/0643; A61N 2005/0645; A61N 2005/0647; A61N 2005/0648; A61N 2005/065; A61N 2005/0651; A61N 2005/0652; A61N 2005/0658; A61N 2005/0659; A61N 2005/066; A61N 2005/0662; A61N 2005/0663; A61N 2005/0664; A61N 2005/0667

See application file for complete search history.

(56) References Cited

U.S. PATENT DOCUMENTS

| | | | |
|---|---|---|---|
| 5,568,208 | A | 10/1996 | Van De Velde |
| 5,755,752 | A | 5/1998 | Segal |
| 6,033,431 | A | 3/2000 | Segal |
| 6,254,596 | B1 | 7/2001 | Lawandy |
| 6,319,273 | B1 | 11/2001 | Chen |
| 6,385,221 | B1 | 5/2002 | Neuberger |
| 6,421,361 | B1 | 7/2002 | Neuberger |
| 6,507,758 | B1 | 1/2003 | Greenberg |
| 6,599,891 | B2 | 7/2003 | North |
| 6,648,876 | B2 | 11/2003 | Murakami |
| 6,676,655 | B2 | 1/2004 | McDaniel |
| 6,800,086 | B2 | 10/2004 | Strong |
| 6,808,523 | B2 | 10/2004 | Fujisaka |
| 6,986,782 | B2 | 1/2006 | Chen |
| 7,015,240 | B2 | 3/2006 | North |
| 7,018,395 | B2 | 3/2006 | Chen |
| 7,158,555 | B2 | 1/2007 | Momiuchi |
| 7,288,106 | B2 | 10/2007 | Heacock |
| 7,311,723 | B2 | 12/2007 | Seibel |
| 7,331,954 | B2 | 2/2008 | Temelkuran |
| 7,354,432 | B2 | 4/2008 | Eells |
| 7,479,136 | B2 | 1/2009 | Dotson |
| 7,682,027 | B2 | 3/2010 | Buczek |
| 7,744,590 | B2 | 6/2010 | Eells |
| 7,766,903 | B2 | 8/2010 | Blumenkranz |
| 7,794,453 | B2 | 9/2010 | Zemmouri |
| 7,883,535 | B2 | 2/2011 | Cantin |
| 7,980,745 | B2 | 7/2011 | Shanbaky |
| 7,991,258 | B2 | 8/2011 | Temelkuran |
| 8,105,321 | B2 | 1/2012 | Zemmouri |
| 8,109,981 | B2 | 2/2012 | Gertner |
| 8,180,444 | B2 | 5/2012 | Neuberger |
| 8,251,982 | B2 | 8/2012 | Zaghetto |
| 8,292,434 | B2 | 10/2012 | Horvath |
| 8,315,280 | B2 | 11/2012 | Zimare |
| 8,945,197 | B1 | 2/2015 | Friend |
| 9,592,404 | B2 | 3/2017 | Dotson |
| 2005/0244469 | A1 | 11/2005 | Whitcup |
| 2006/0184214 | A1 | 8/2006 | McDaniel |
| 2007/0123844 | A1 | 5/2007 | Henry |
| 2008/0102122 | A1 | 5/2008 | Mahadevan |
| 2010/0241196 | A1* | 9/2010 | Meyer |
| 2012/0088980 | A1 | 4/2012 | Gravely |
| 2013/0304162 | A1* | 11/2013 | Veres |
| 2013/0317570 | A1 | 11/2013 | Luttrull |
| 2014/0036511 | A1 | 2/2014 | Whitfield et al. |
| 2014/0158541 | A1* | 6/2014 | Beaudet |
| 2015/0057701 | A1 | 2/2015 | Kelleher |
| 2016/0067086 | A1 | 3/2016 | Tedford |
| 2016/0067087 | A1* | 3/2016 | Tedford |
| 2016/0166853 | A1 | 6/2016 | Dotson |
| 2016/0317833 | A1 | 11/2016 | Tedford |
| 2016/0356475 | A1 | 12/2016 | Honda et al. |
| 2017/0185042 | A1* | 6/2017 | Yuen |

FOREIGN PATENT DOCUMENTS

| | | |
|---|---|---|
| WO | 2012123709 A1 | 9/2012 |
| WO | 2015011589 A1 | 1/2015 |
| WO | 2015073259 A3 | 5/2015 |
| WO | 2016049669 A1 | 4/2016 |
| WO | 2017004257 A1 | 1/2017 |

OTHER PUBLICATIONS

U.S. Appl. No. 13/679,557, filed Nov. 16, 2012, "Ophthalmic Phototherapy Device and Associated Treatment Method".
U.S. Appl. No. 15/050,484, filed Feb. 23, 2016, "Ophthalmic Phototherapy Device and Associated Treatment Method".
U.S. Appl. No. 15/050,483, filed Feb. 23, 2016, "Ophthalmic Phototherapy Device and Associated Treatment Method".
U.S. Appl. No. 15/050,482, filed Feb. 23, 2016, "Ophthalmic Phototherapy Device and Associated Treatment Method".
EP Search Report dated Jun. 24, 2020 for corresponding EP Application No. 18840919.7.

* cited by examiner

SYSTEM AND METHOD FOR DIRECTING LIGHT INTO A PATIENTS EYE

CROSS-REFERENCE TO RELATED APPLICATIONS

This application is a national stage entry of PCT Appl. No. PCT/US18/44954, filed Aug. 2, 2018, entitled "SYSTEM AND METHOD FOR DIRECTING LIGHT INTO A PATIENT'S EYE", which claims the benefit of U.S. Provisional Application No. 62/540,204, filed Aug. 2, 2017, entitled "SYSTEM AND METHOD FOR TREATMENT AND PREVENTION OF VISION DISORDERS USING LIGHT TREATMENT". This provisional application is hereby incorporated by reference in its entirety for all purposes.

TECHNICAL FIELD

The present disclosure relates generally to treating disorders of the eye and, more specifically, to systems and methods that direct light into a patient's eye to treat a disorder of the eye.

BACKGROUND

One example of an eye disorder is macular edema. Macular edema causes distorted vision due to a buildup of fluid in the macula due to damaged blood vessels in the retina. Common causes of blood vessel damage in the retina include diabetic retinopathy, age-related macular degeneration, and cataract surgery. Diabetic retinopathy is the leading cause of macular edema, affecting up to 80% of the diabetic population in the US, and is a leading cause of blindness if left untreated.

Current treatments for macular edema involve first trying to treat the underlying cause, such as diabetes, and then directly treating the damage in the retina. The standard treatment for the damage in the retina is laser surgery to seal leaking blood vessels in the retina. However, laser surgery requires a long recovery time (between 3-6 months) and, even after the long recovery time, does not always improve the patient's vision. Other treatments for the damage in the retina include virectomy, anti-inflammatory treatments, and injections of anti-vascular endothelial growth factor. The above-mentioned treatments are invasive and risk failing to treat the macular edema and creating further vision problems. A low-cost and effective alternative or adjunctive treatment would greatly improve the treatment outcomes of patient's with macular edema and many other disorders of the eye.

SUMMARY

The present disclosure relates generally to treating disorders of the eye and, more specifically, to systems and methods that direct light into a patient's eye to treat a disorder of the eye.

In one aspect, the present disclosure can include a method for directing light into a patient's eye to treat a disorder of the eye. A device can be placed proximal to a patient's eye. The device can include a printed circuit board that includes an array of light delivery devices. The device can also include a lens that includes a plurality of ridges that provide a heat sink for the array of light delivery devices. The light delivery devices can be powered to generate light. The light can be directed into the patient's eye regardless of a position of the patient's eye.

In another aspect, the present disclosure can include a system that directs light into a patient's eye to treat a disorder of the eye. A device can be configured for placement over a patient's eye socket to deliver light into the patient's eye. The device can include a printed circuit board that includes an array of light delivery devices to provide the light. The device can also include a lens (which may be a flexible lens). The lens can include a plurality of ridges that provide a heat sink for the light delivery devices. A controller can provide power to the printed circuit board.

BRIEF DESCRIPTION OF THE DRAWINGS

The foregoing and other features of the present disclosure will become apparent to those skilled in the art to which the present disclosure relates upon reading the following description with reference to the accompanying drawings, in which.

DETAILED DESCRIPTION

I. Definitions

Unless otherwise defined, all technical terms used herein have the same meaning as commonly understood by one of ordinary skill in the art to which the present disclosure pertains.

In the context of the present disclosure, the singular forms "a," "an" and "the" can also include the plural forms, unless the context clearly indicates otherwise.

As used herein, the terms "comprises" and/or "comprising" can specify the presence of stated features, steps, operations, elements, and/or components, but do not preclude the presence or addition of one or more other features, steps, operations, elements, components, and/or groups.

As used herein, the term "and/or" can include any and all combinations of one or more of the associated listed items.

Additionally, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or acts/steps) is not limited to the order presented in the claims or figures unless specifically indicated otherwise.

As used herein, the term "eye" refers to an organ of sight. The eye has a number of components including, but not limited to, the cornea, iris, pupil lens, retina, macula, optic nerve, choroid, and vitreous. When light is referred to as being directed through the eye, the light is directed into the pupil to reach the retina and/or macula.

As used herein, the term "retina" refers to a nerve layer that lines the back of the eye, senses light and creates impulses that travel through the optic nerve to the brain. In other words, the retina receives light and converts the light to a neural signal.

As used herein, the term "macula" refers to a small area of the retina that contains special light-sensitive cells and allows for vision of fine details.

As used herein, the term "optic nerve" refers to the nerve that transmits visual information from the retina to the brain.

As used herein, the term "disorder of the eye" refers to any anatomic and/or functional pathological manifestation related to the eye that affects vision. More specifically, the pathological manifestation can be related to the optic nerve, the retina and/or the macula. Examples of disorders of the eye include, but are not limited to, macular degeneration, retinopathy, diabetic eye disease, optic neuropathy, amblyopia, induced retinal damage, and the like.

As used herein, the term "photobiomodulation" refers to the application of a light signal to a portion of a subject's body to induce a phototherapeutic response in cells within the portion of the subject's body.

As used herein, the term "photobiomodulation therapy (PBMT)" refers to a drug-free, non-invasive treatment procedure, in which a light signal is applied to the subject's eye to treat a certain medical condition (e.g., disorder of the eye).

As used herein, the terms "light" and "light signal" can be used interchangeably to refer to light having at least one wavelength from 500 nm to 1100 nm. However, the light may include a combination of wavelengths that create a synergistic effect when combined.

As used herein, the term "printed circuit board" refers to a mechanism to mechanically support and electrically connect electrical components (like light delivery devices) using conductive tracks, pads, and other features etched from one or more sheet layers of a conductive material (like copper) laminated onto and/or between sheet layers of a non-conductive substrate. The printed circuit board can be rigid and/or flexible.

As used herein, the term "light delivery device" refers to an electrical component that can provide light at least one wavelengths upon receiving an electrical signal. For example, the light source can be a low-level laser source (e.g., a laser light emitting diode (LED)) that generates coherent light). As another example, the light source can be an incoherent light source, such as a traditional LED.

As used herein, the term "proximal" refers to a location that is near a target. For example, a device that is located proximal at least a portion of the eye can be located over the at least the portion of the eye, but need not be directly over the center of the area in the at least the portion of the eye.

As used herein, the term "sufficient" refers to an amount adequate enough to satisfy a condition. For example, "a time sufficient to stimulate a phototherapeutic response in at least a portion of the eye" can refer to a light signal being applied to at least a portion of the eye for a time adequate enough to stimulate the phototherapeutic response.

As used herein, the terms "subject" and "patient" can be used interchangeably and refer to any warm-blooded organism including, but not limited to, a human being, a pig, a rat, a mouse, a dog, a cat, a goat, a sheep, a horse, a monkey, an ape, a rabbit, a cow, etc.

II. Overview

The present disclosure relates to treating disorders of the eye. Previously, treatments for disorders of the eye have included laser surgery, which has a long associated recovery time and, even after the long recovery time, may not always improve a patient's vision. Other treatments include virectomy, which is invasive and may cause additional problems, and pharmaceutical therapy, which may provide only temporary relief or be entirely ineffective. Photobiomodulation therapy (PBMT) applied alone or in combination with these previous treatments has been shown to be a safe, beneficial treatment for the eye at a low cost. Even with its clear advantages, PBMT has not been widely used in the treatment of disorders of the eye. In fact, no personal device exists due to concerns related to safety, personal use, extended use, ergonomics, and portability. Most notably, previous devices have been ineffective at delivery PBMT into the eye. When a patient's eye moves naturally, previous devices have been unable to compensate for this movement, rendering these devices ineffective to deliver the PBMT into the eye.

The present disclosure provides a device that directs the light of PBMT into the patient's eye, no matter if the eye moves. The device can be configured for placement over the patient's eye socket to deliver the light into the patient's eye and can be used in the clinic and/or by the patient at home. Notably, the device can include a printed circuit board that includes an array of light delivery devices to provide the light and a lens. The device can provide a uniform distribution of light so that no matter how the patient's eye moves, the correct dose of light enters the eye. Additionally, the device can provide a safety feature because the lens can include a plurality of ridges that provide a heat sink for the light delivery devices. Accordingly, the present disclosure relates more specifically, to systems and methods that that direct light into a patient's eye to treat a disorder of the eye using the specially-configured device.

III. Photobiomodulation Therapy (PBMT)

Photobiomodulation therapy (PBMT) can provide a low-cost and effective alternative or adjunctive treatment for a disorder of the eye. When used on the eye, the light used for PBMT can have one or more wavelengths between 500 nm and 1100 nm and an energy density of 20 mW/cm2 to 75 mW/cm$^2$ applied for a time (e.g., between 30 seconds and 5 minutes). In some instances, two or more wavelengths can be combined for a single PBMT treatment. The unique device configured to cover at least a portion of a patient's eye socket and direct the light through the pupil and into the eye. The device includes a printed circuit board with an array of light delivery devices arranged to direct the light through the pupil. The device also includes a lens that includes a plurality of ridges that provide a heat sink for the array of light delivery devices.

The light of PBMT has been shown to have a modulatory effect on retinal cells (including photoreceptors and other cells of the retina, such as support cells) based on the principle that certain molecules in living systems absorb photons and trigger signalling pathways in response to light. When a photon of light is absorbed by a chromophore in a cell, an electron in the chromophore can become excited and jump from a low-energy orbit to a higher-energy orbit. This stored energy then can be used by the living system to perform various cellular tasks. While not wishing to be bound by theory, there is strong evidence to suggest that one of the basic cellular tasks mechanisms of transcranial PBMT is the acceleration of electron transfer by electromagnetic radiation in the visible and near infrared region of the spectrum, via the modulation of cytochrome c-oxidase ("CCO") activity in retinal cells.

CCO is the primary photo acceptor of visible to near infrared light energy and is the enzyme responsible for catalysing oxygen consumption in cellular respiration and for the production of nitric oxide under hypoxic conditions. High-energy electrons are passed from electron carriers through a series of trans-membrane complexes (including CCO) to the final electron acceptor, generating a proton gradient that is used to produce adenosine triphosphate (ATP). The application of light directly results in ATP production and electron transport. In short, the application of PBMT can increase ATP production, down-regulate cellular respiration modulated by NO, and promotes the metabolism of oxygen, while increasing the production of reactive oxygen species (ROS).

IV. Systems

One aspect of the present disclosure can include a system 10 (FIG. 1) that directs light into a patient's eye. The system 10 includes a controller 12 and a PBMT device 14. The controller 12 can provide power to the PBMT device 14, which can generate the light and can be configured to direct the light into the patient's eye. At least a portion of the PBMT device 14 can be configured for placement over and/or proximal to the patient's eye. The PBMT device 14 can be in the form of a patch, a light bridge, glasses, or the like. Additionally, the PBMT device may be coupled to an anchor, like a strap, to hold the PBMT device in place proximal to the patient's eye.

Figure 1:
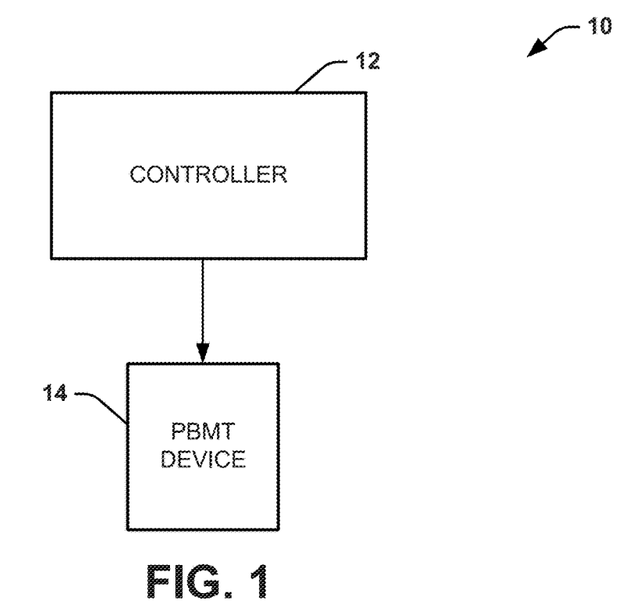
FIG. 1 is a block diagram illustration showing an example of a system that directs light into a patient's eye in accordance with an aspect of the present disclosure.

The controller 12 can provide power to at least a portion of the PBMT device 14, which can generate light when powered. The PBMT device can be shaped to direct the light into (or through) the patient's eye. An advantage of the system 10 compared to conventional light delivery solutions is that the PBMT device 14 is configured to direct the light into the patient's eye regardless of the orientation of the patient's eye. This allows the patient's eye to receive the benefits of PBMT described above. The system 10 is designed so the patient can receive the PBMT either in the clinic or at home. To this end, the PBMT device 14 can be can be dust tight and waterproof (e.g., at least IP 65).

Figure 2:
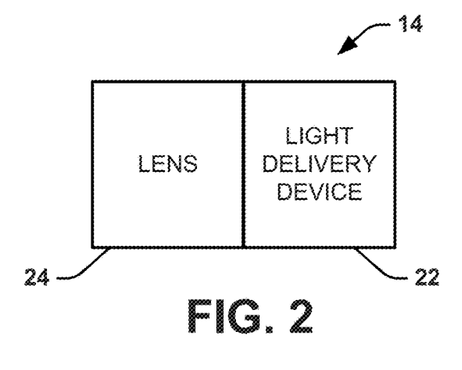
FIG. 2 is a block diagram illustration showing an example of the PBMT device of FIG. 1.

The PBMT device 14 can include at least a light delivery device 22 that generates the light and a lens 24 that facilitates delivery of the light, as shown in FIG. 2. Note that the PBMT device 14 can include additional components to facilitate the delivery of the light through the patient's eye. The PBMT device 14 can be shaped further ensure delivery of the light through the patient's eye. At least a portion of the lens 24 and/or the light delivery device 22 can be flexible. However, in some instances, at least a portion of the lens 24 and/or the light delivery device 22 can be rigid.

Figure 3:
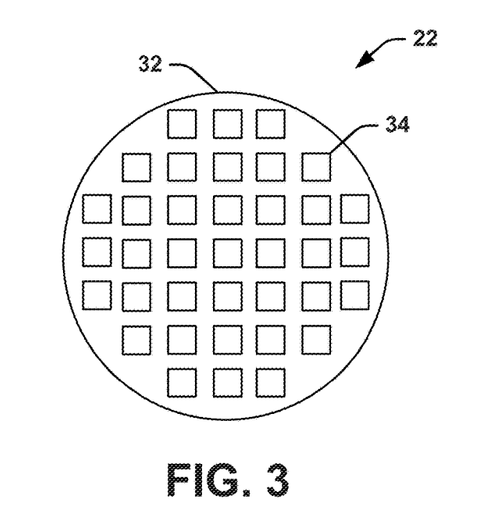
FIG. 3 is a block diagram illustration showing an example light delivery device of FIG. 2.

An example of the light delivery device 22 is shown in FIG. 3. The light delivery device 22 can include an array of light delivery devices 34 (e.g., one or more) arranged regularly on a printed circuit board 32. The light delivery devices 34 can be light emitting diodes, laser diodes, or the like. In some instances, the light delivery devices 34 can each (individually) generate light with a wavelength from 500 nm to 1100 nm. In other instances, the light delivery devices 34 can each (individually) generate light with a wavelength from 630 nm to 670 nm or from 800 nm to 900 nm. The regular arrangement of the light delivery devices 34 with uniform spacing can contribute to the uniform delivery of light (in other words, the light is delivered at a uniform density). Each of the light delivery devices 34 can deliver a unique light signal from a unique position. The printed circuit board 32 can be flexible and/or rigid.

Figure 4:
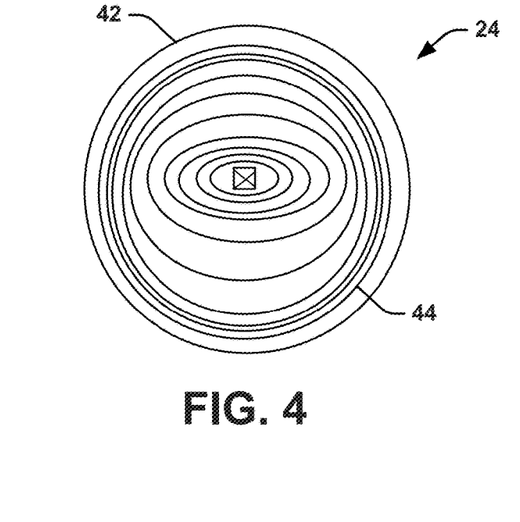
FIG. 4 is a diagram illustration showing an example lens of FIG. 2.

An example of the lens 24 is shown in FIG. 4. The lens 24 can be flexible and can overlay the light delivery device 22 to facilitate delivery of the light through the eye. The lens 24 can include a base 42 and a plurality of ridges 44 that provide a heat sink for the light delivery devices 34. The heat sink absorbs heat from the light delivery devices 34 so that the heat is not transmitted to the eye. At least a portion of the lens 24 can be injected with an antimicrobial or antibacterial element or compound (such as one containing silver). The lens 24 can be constructed of any material that facilitates delivery of light (e.g., silicon, silicone, etc.).

The controller 12 of system 10 can deliver power according to a wired connection and/or a wireless connection. The controller 12 can include an internal battery and/or external power receiver/storage to provide power to at least a portion of the electronics of the PBMT device 14 required for operation of the system 10. In some instances, the controller 12 can be a unit external to the PBMT device 14 (e.g., similar to a TENS device). In other instances, the controller 12 can be included with the PBMT device 14 (e.g., in the periphery of the PBMT device 14). In still other instances, the controller 12 can be located on or within a device proximal to the PBMT device (e.g., a strap device).

The controller 12 can receive and/or provide AC and/or DC current. Notably, the controller can include a log generator that is only accessible to previously approved users (e.g., a doctor or hospital). The previously approved users can be associated with user names associated with permissions that allow access to the logs. However, the logs can be transmitted to computers associated with the permitted users. The logs can include data related to user of the PBMT—such as when, where, how often, and the like.

Figure 5:
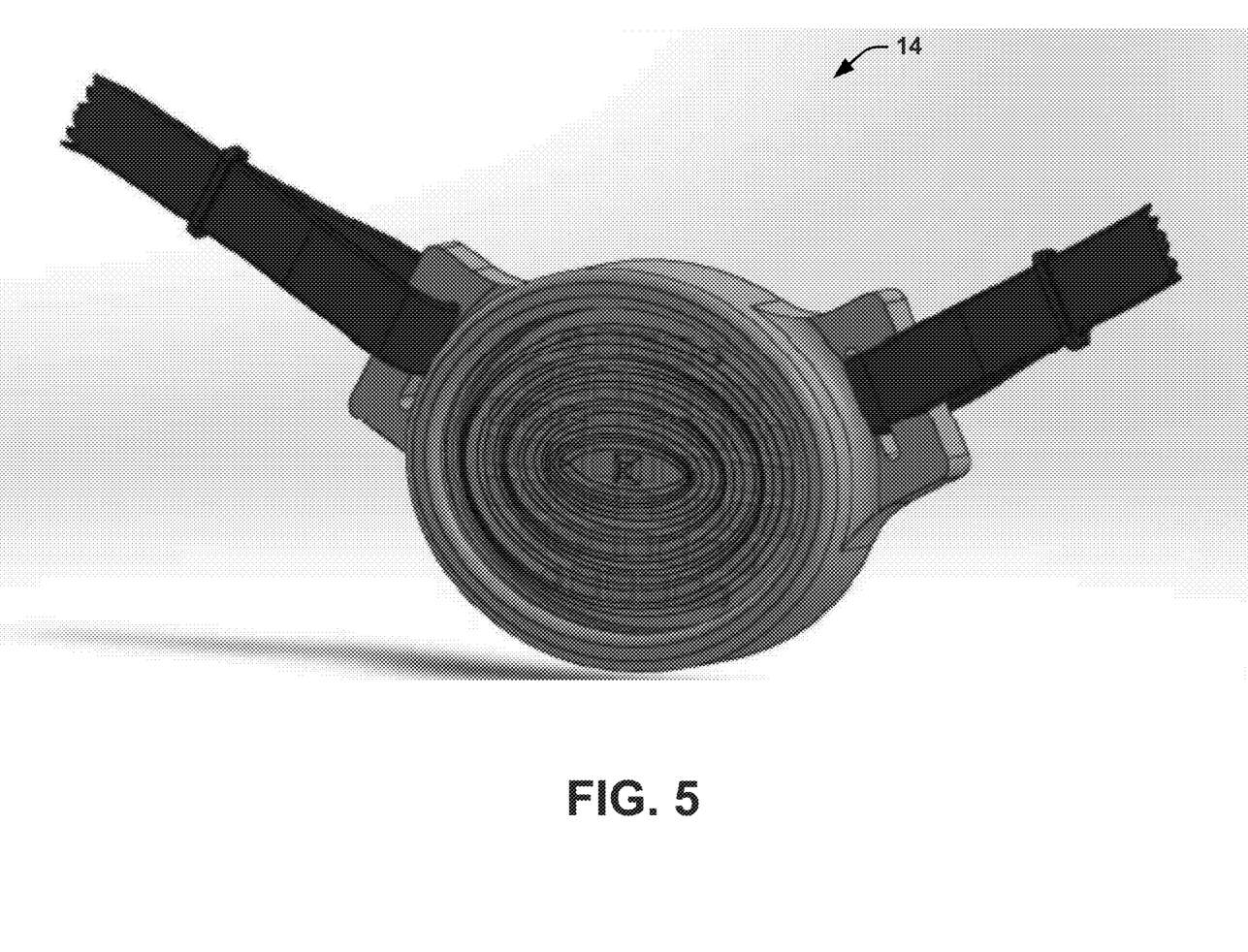
FIG. 5-6 illustrate an example device that can be used to implement the system of FIG. 1.
Figure 6:
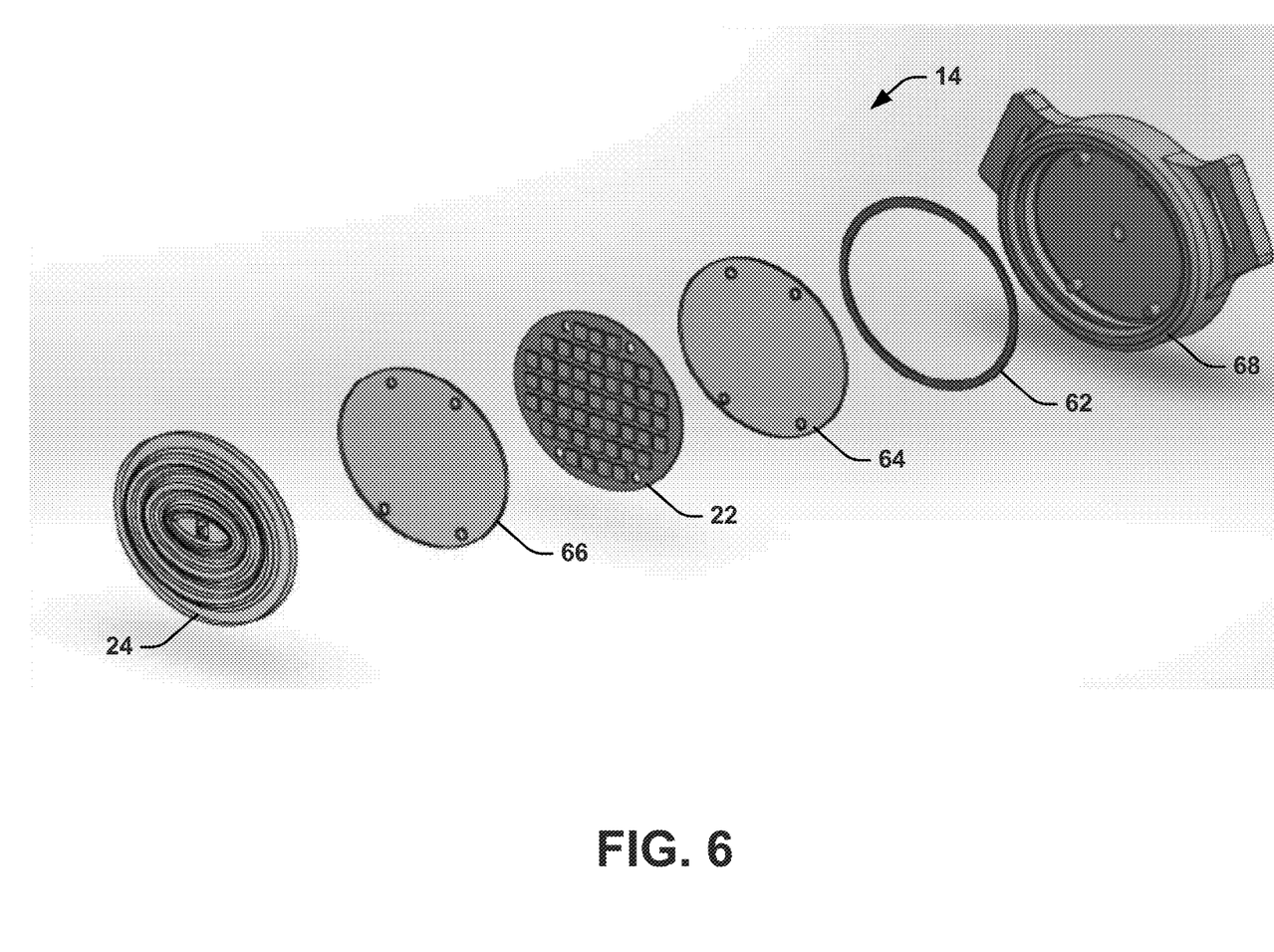

FIGS. 5 and 6 provide an illustration of an example PBMT device 14 that can be used in the system 10. FIG. 5 provides a view from an eye looking through the lens to receive the PBMT. This PBMT device 14 can include a strap to anchor the device in position over the eye. FIG. 6 shows the components of the device shown in FIG. 5. The lens 24 (shaped to the eye, made of silicon with concentric rings) and the light delivery device 22 (flexible design) are separated by a MYLAR layer 66 made of a MYLAR sheet to further facilitate the homogeneous, uniform density of light (to facilitate diffusion of the light). Another MYLAR layer 64 is located behind the light delivery device 22. The device also includes a flexible metallic ring 62 to conform the lens 24 and the light delivery device 22 to a shape of the patient's eye to direct the light through the patient's eye and into the patient's pupil. The device also includes a component 68 to anchor the layers therewithin. As shown in FIGS. 5 and 6, the component 68 can mate with the anchor (in this case the strap). Moreover, the component 68 can be opaque to better focus the light into the patient's eye. Each of the layers 24, 66, 22, and 64 can include holes to attach to pegs within the component 68.

V. Methods

Figure 7:
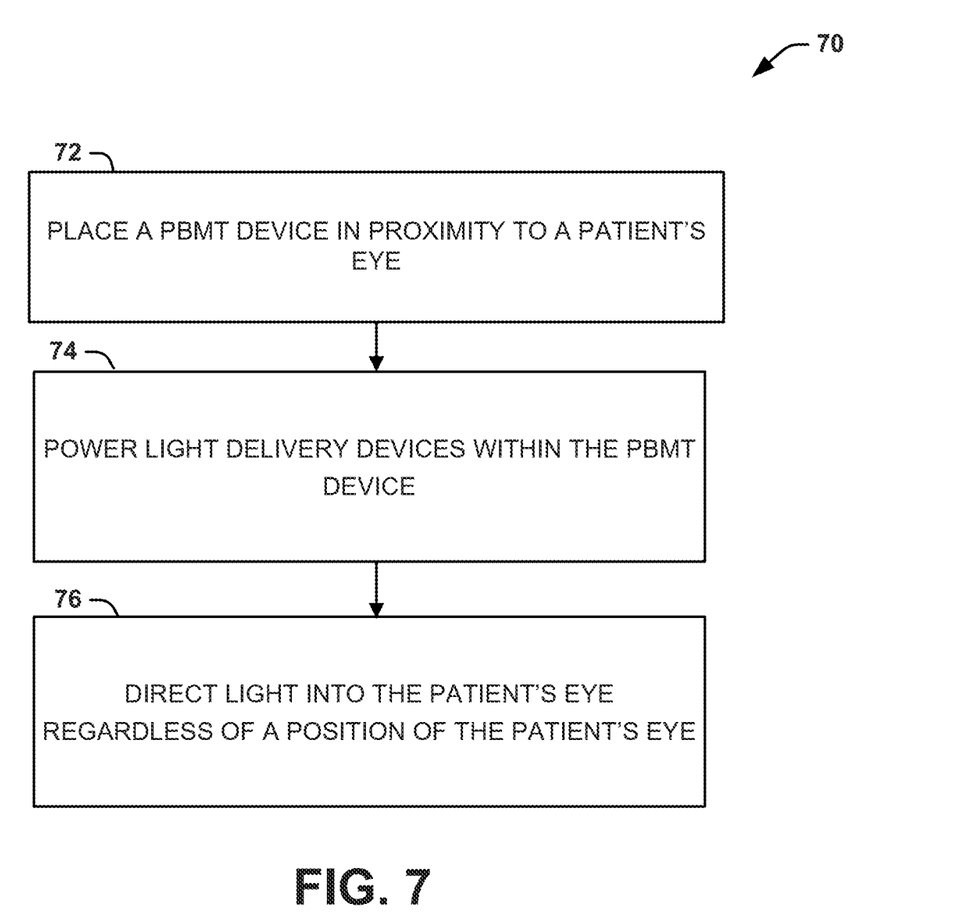
FIG. 7 is a process flow diagram of an example method for directing light into a patient's eye to treat a disorder of the eye in accordance with another aspect of the present disclosure.

Another aspect of the present disclosure can include a method 70 (FIG. 7 for directing light into a patient's eye to treat a disorder of the eye. The method 70 can be executed by hardware—for example, at least a portion of the system 10 shown in FIG. 1 and described above. The method 70 is illustrated as process flow diagrams with flowchart illustrations. For purposes of simplicity, the method 70 is shown and described as being executed serially; however, it is to be understood and appreciated that the present disclosure is not limited by the illustrated order as some steps could occur in different orders and/or concurrently with other steps shown and described herein. Moreover, not all illustrated aspects may be required to implement the method 70. Additionally, one or more elements that implement the methods 70, such as PBMT device 13, the controller 12 of FIG. 1, may include a non-transitory memory and one or more processors that can facilitate the configuration and generation of the light of PBMT.

At step 72, a PBMT device can be placed in proximity to a patient's eye. In some instances, the PBMT device can cover at least a portion of the patient's eye. In other instances, the PBMT device can cover the entire eye socket of the patient. As one example, the PBMT device can be in the form of an eye patch. However, the PBMT device can take the form of one or more different examples, such as glasses, goggles, a light bridge, or any other device that can be placed in proximity to the patient's eye. The PBMT device can also include a mechanism to hold the PBMT device in place in proximity to the patient's eye, like a strap.

The PBMT device can be dust tight and waterproof (e.g., at least IP 65). The PBMT device can include a printed circuit board, having an array of light delivery devices. The printed circuit board can be flexible and/or rigid. The array of light delivery devices can deliver light at a uniform density. The light delivery devices are light emitting diodes and/or laser emitting diodes. The light delivery devices can each provide light with a wavelength from 500 nm to 1100 nm. As a more specific example, the light delivery devices can each provide light with a wavelength from 630 nm to 670 nm or 800 nm to 900 nm. The PBMT can also include a lens, laid over the PBMT device, having a plurality of ridges that provide a heat sink for the light delivery devices. In some instances, the PBMT device can include a flexible metallic ring to conform the printed circuit board and/or the lens to direct the light through the patient's eye into the patient's pupil. Additionally or alternatively, the PBMT can include at least one MYLAR sheet to further facilitate the homogeneous uniform density of light.

At step 74, light delivery devices within the PBMT device can be powered. The power can be supplied by a controller device. When powered, the light delivery devices can generate the light. The light can be delivered for a predetermined time (e.g., from 30 seconds-5 minutes). Notably, the light delivery devices are arranged on the printed circuit board to enable the uniform density of light. The power can be provided by the controller device, which can receive and/or supply AC and/or DC current. The controller can include a power source (e.g., a battery, such as a rechargeable battery). In some instances, the controller can include a data mining capability to populate a log generator to record when, where, and how often the patient utilizes the PBMT device.

At step 76, the light can be directed into the patient's eye regardless of a position of the patient's eye. The uniform distribution of light ensures that the proper dose of light travels through the pupil. In fact, the uniform distribution of light ensures that light enters through the pupil regardless of the orientation of the patient's eye.

From the above description, those skilled in the art will perceive improvements, changes and modifications. Such improvements, changes and modifications are within the skill of one in the art and are intended to be covered by the appended claims. All patents, patent applications, and publications cited herein are incorporated by reference in their entirety.

The invention claimed is:

1. A system comprising:
a device configured for placement over at least a portion of a patient's eye socket to deliver light into the patient's eye, wherein the device comprises an eyepatch device configured to attach to the patient's head to cover at least a portion of the patient's eye, the device comprising:
a printed circuit board comprising an array of light delivery devices to provide the light;
a lens comprising a plurality of ridges that provide a heat sink for the light delivery devices;
a flexible metallic ring to conform the printed circuit board and the lens to the patient's eye and to direct the light through the patient's eye and into the patient's pupil; and
at least one MYLAR sheet to facilitate a homogeneous uniform density of light from the printed circuit board; and
a controller to power the printed circuit board.

2. The system of claim 1, wherein the array of light delivery devices comprises light emitting diodes or laser diodes that provide light with at least one wavelength from 500 nm to 1100 nm.

3. The system of claim 1, wherein the array of light delivery devices comprises light emitting diodes or laser diodes that provide light with at least one wavelength from 630 nm to 670 nm or from 800 nm to 900 nm.

4. The system of claim 1, wherein the lens delivers the light at a uniform density.

5. The system of claim 1, wherein the light delivery devices are arranged on the printed circuit board with a uniform spacing.

6. The system of claim 1, wherein the controller is at least one of built into the device, housed in a strap proximal to the device, or external to the device.

7. The system of claim 1, wherein the controller comprises a power source, a non-transitory memory, and a processor, and communicates with the printed circuit board according to a wired connection or a wireless connection.

8. The system of claim 1, wherein the controller records information related to a patient's use of the device,
wherein the information related to the patient's use of the eyepatch device is secure and available by a computing device associated with an authorized user.

9. The system of claim 1, wherein an antimicrobial material is embedded within the lens.

10. The system of claim 9, wherein the antimicrobial material comprises silver.

11. The system of claim 1, wherein the device is dust tight and waterproof.

12. A method comprising:
placing a device proximal to at least a portion of a patient's eye, wherein the device comprises:
a printed circuit board comprising an array of light delivery devices;
a lens comprising a plurality of ridges that provide a heat sink for the light delivery devices;
a flexible metallic ring to conform the printed circuit board and the lens to direct the light through the patient's eye and into the patient's pupil; and
at least one MYLAR sheet to facilitate a homogeneous uniform density of light;
powering the light delivery devices to generate the light; and
directing the light into the patient's eye regardless of a position of the patient's eye.

13. The method of claim 12, wherein the array of light delivery devices comprises light emitting diodes or laser diodes that provide light with at least one wavelength from 500 nm to 1100 nm.

14. The method of claim 12, further comprising delivering the light at a uniform density.

15. The method of claim 14, wherein the light is delivered for a predetermined time.

16. The method of claim 15, wherein the predetermined time is from 30 seconds to 5 minutes.

* * * * *